United States Patent
Orjales Venero et al.

(10) Patent No.: US 7,612,095 B2
(45) Date of Patent: Nov. 3, 2009

(54) POLYMORPH OF 4-[2-[4-[1-(2-ETHOXYETHYL)-1H-BENZIMIDAZOLE-2-YL]-1-PIPERIDINYL] ETHYL]-αα-DIMETHYL-BENZENEACETIC ACID

(75) Inventors: Aurelio Orjales Venero, Neguri (ES); Maravillas Bordell Martin, Leioa (ES); Gonzalo Canal Mori, Leioa (ES); Haydee Blanco Fuente, Las Arenas (ES); Maria Luisa Lucero De Pablo, Algorta (ES); Victor Rubio Royo, Getxo (ES); Ramon Mosquera Pestaña, Las Arenas (ES)

(73) Assignee: Faes Farma, S.A. (ES)

( * ) Notice: Subject to any disclaimer, the term of this patent is extended or adjusted under 35 U.S.C. 154(b) by 505 days.

(21) Appl. No.: 10/511,822

(22) PCT Filed: Apr. 19, 2002

(86) PCT No.: PCT/ES02/00194

§ 371 (c)(1),
(2), (4) Date: Mar. 23, 2005

(87) PCT Pub. No.: WO03/089425

PCT Pub. Date: Oct. 30, 2003

(65) Prior Publication Data

US 2005/0203141 A1    Sep. 15, 2005

(51) Int. Cl.
*A61K 31/454* (2006.01)
*C07D 43/04* (2006.01)

(52) U.S. Cl. ....................... 514/322; 546/199

(58) Field of Classification Search ................. 514/322; 546/199

See application file for complete search history.

(56) References Cited

U.S. PATENT DOCUMENTS 5,877,187 A * 3/1999 Orjales et al. ............... 514/322

FOREIGN PATENT DOCUMENTS

EP        0 818 454 A1    1/1998

OTHER PUBLICATIONS

Otsuka et al. "Effect of polymorphic . . . " Chem. Pharm. bull 47(6)852-856 (1999).*
Taday et al. "Using terahertz . . . " J. Pharm. sci. v.92(4) p. 831-838 (2003).*
Kirk-Othmer Encyclopedia of Chemical Technology,John Wiley & Sons, Inc., pp. 95-147, Article Online Posting Date: Aug. 16, 2002.*
Rowland and Tozer "Clinical pharmacokinetics . . . " p. 132 (1995).*
Corcostegui et al. "Prelinical pharmacology . . . " Drug R D 6(6) p. 371-384 (2005).*
Corcostegui et al. "In vivo pharmacological . . . " Crug R D 7(4) p. 219-231 (2005).*
Cheronis "Semimicro experimental organic chemistry" p. 31-35 (1958).*
Muzaffar et al. "Polymorphism and drug availability" J. Phar. 1(1) 59-66 (1979).*
Jain et al. "Polymorphisom in pharmacey" Indian Drugs 23(g)315-329 (1986).*
Doelker et al. "Crystalline modification . . . " CA 138:209993 (2002.*
Doelker et al. "Physicochemical behavior or active . . . " CA 132:325872 (2000).*
Corcostegui et al. "In vivo pharmacological . . . " Drug R D 7(4) p. 219-231 (2005).*
Lanz "Pharmaceutical powder tecnology . . . " Basal (2006) p. 1-4.*
CMU Pharmaceutical polymorphism, internet print out (2008) p. 1-3.*
Berrueta, L.A., "Matrix solid-phase dispersion technique for the determination of a new antiallergic drug, bilastine, in rat faeces" *Journal of Chromatography B.*, 760:185-190 (2001).
International Search Report dated Oct. 31, 2002.

* cited by examiner

*Primary Examiner*—Celia Chang
(74) *Attorney, Agent, or Firm*—Ostrolenk Faber LLP

(57) ABSTRACT

Crystalline form 1 of 4-[2-[4-[1-(2-ethoxyethyl)-1H-benzimidazole- 2-yl]-1 -piperidinyl] ethyl]-αα- dimethyl-benzen⊖eacetic acid Crystalline form 1 of 4-[2-[4-[1-(2-ethoxyethyl)-1H-benzimidazole-2-yl]-1 -piperidinyl]ethyl]-αα-dimethyl-benzen⊖eacetic acid of formula (I) is described, procedures for its preparation, pharmaceutical formulae containing crystalline form 1 and the use of crystalline form 1 to treat allergic reactions and pathological processes mediated by histamine in mammals such as man.

(I)

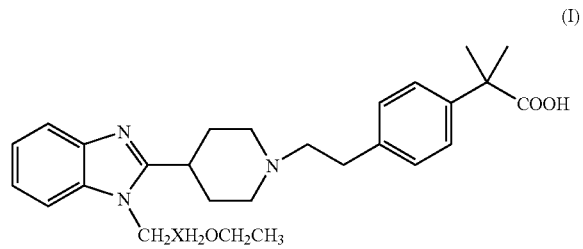

6 Claims, 3 Drawing Sheets

POLYMORPH OF 4-[2-[4-[1-(2-ETHOXYETHYL)-1H-BENZIMIDAZOLE-2-YL]-1-PIPERIDINYL]ETHYL]-αα-DIMETHYL-BENZENEACETIC ACID

CROSS-REFERENCE TO RELATED APPLICATION

This is a U.S. national stage application of PCT/ES02/00194- filed 19 Apr. 2002. The PCT International application was published in the Spanish language.

AREA OF THE INVENTION

The invention refers to a new crystalline form of 4-[2-[1-(2-ethoxyethyl)-1H-benzidimazole-2-yl]-1-piperidinyl] ethyl]-αα-dimethyl-benzen⊖acetic acid (herein referred to as "bilastine") of formula (I).

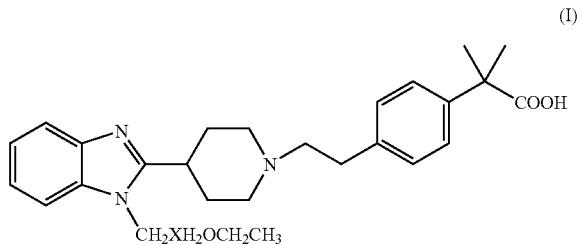

From hereon referred to as crystalline form 1, to procedures used to prepare it, to pharmaceutical formulae that contain crystalline form 1 and to the use of crystalline form 1 to treat allergic reactions and pathological processes mediated by histamine in mammals, such as man.

BACKGROUND OF THE INVENTION

U.S. Pat. No. 5,877,187 confers the rights to bilastine, a preparation with antihistaminic properties without sedative or cardiovascular effects. This patent also concerns a procedure to prepare bilastine and the use of this preparation to treat allergic reactions in mammals but it does not include or suggest the possible existence of polymorphic forms of this compound. To prepare pharmaceutical compositions containing bilastine for their administration in mammals and especially in man, in accordance with international health authority specifications, bilastine must be manufactured in the most stable crystalline form possible, especially in a form that has constant physical properties.

SUMMARY OF THE INVENTION

We have found that bilastine can exist in three different crystalline polymorphic forms, each with different physical properties.

The invention refers to crystalline form 1 of bilastine, characterised by X-ray crystallographic analysis, with approximate crystal parameters as follows:

| | |
|---|---|
| Crystallographic system | Monoclinic |
| Spatial group | P2 (1)/c |
| Crystal size | 0.56 × 0.45 × 0.24 mm |
| Cell dimension | a = 23.38 (5) A angstrom   α = 90°<br>b = 8.829 (17) A   β = 90°<br>c = 12.59 (2) A   γ = 90° |
| Volume | 2600 $A^3$ |
| Z, calculated density | 4, 1.184 mg/$m^3$ |

The crystalline form 1 of bilastine is also characterised by its infrared absorption spectrum in potassium bromide tablet that has the following characteristic absorption bands, expressed in reciprocal centimeters;
3430 (s)*; 3057 (w)*; 2970 (s); 2929 (s); 2883 (m)*; 2857 (m); 2797 (w); 1667 (m); 1614 (m); 1567 (w); 1509 (s); 1481 (m); 1459 (vs)*; 1431 (m); 1378 (w); 1346 (m); 1326 (m); 1288 (w); 1254 (m); 1199 (w); 1157 (w); 1121 (vs); 1045 (w); 1020 (w); 1010 (w); 991 (w); 973 (w); 945 (w); 829 (w); 742 (s); 723 (w); 630 (w), * where (w)=weak intensity, (m)=medium intensity, (s)=strong intensity, (vs)= very strong intensity. FIG. 1 represents the infrared spectrum of the crystalline form 1 of the bilastine in a potassium bromide tablet recorded in a Perkin Elmer Spectrum One FTIR spectrophotometer.

DETAILED DESCRIPTION OF THE INVENTION

Figure 1:
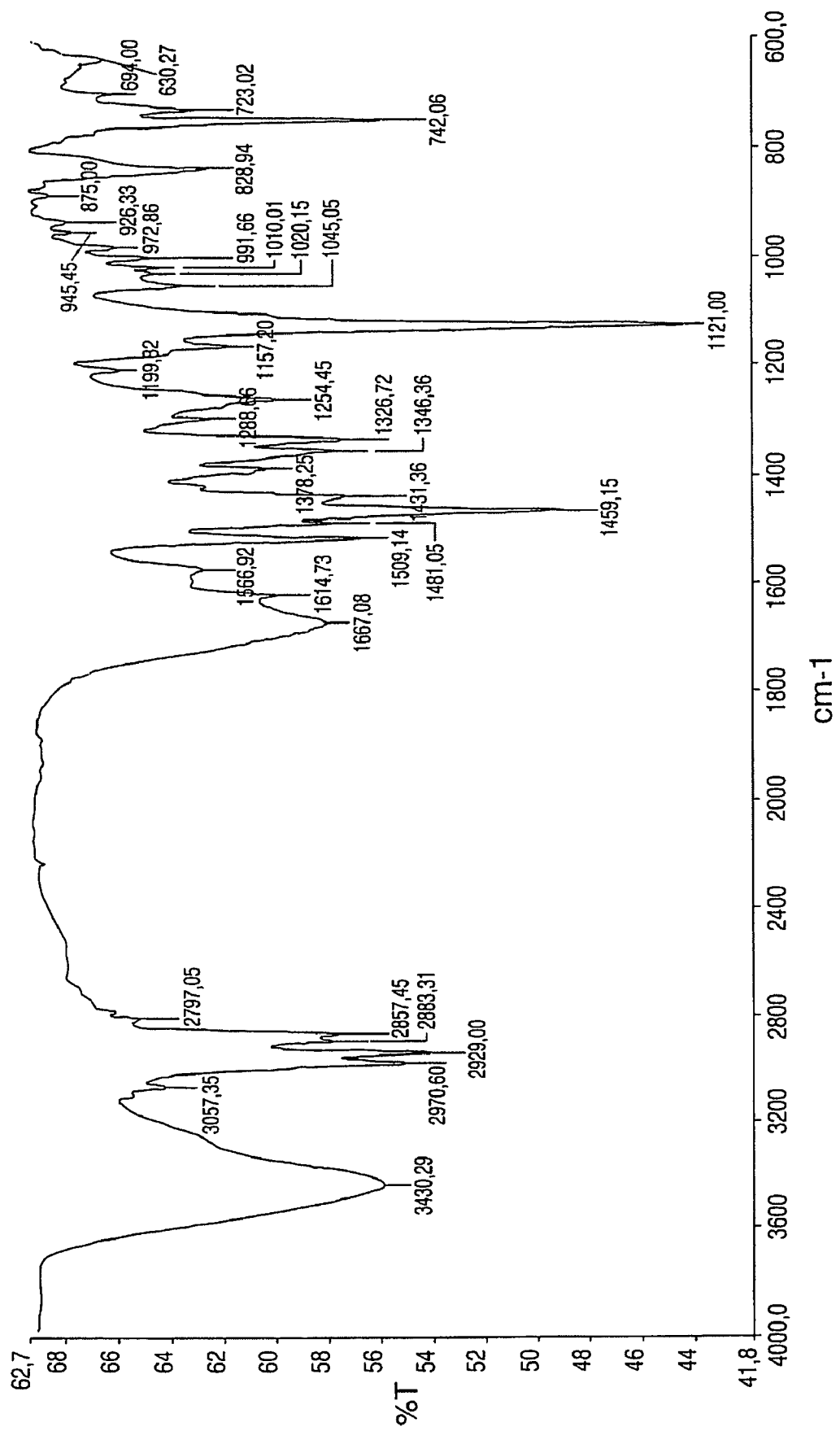
FIG. 1 shows a typical infrared absorption spectrum in potassium bromide of crystalline form 1. (Vertical axis: Transmission (%); Horizontal axis: Wavenumber ($cm^{-1}$)).

We have found that bilastine can exist in three clearly different polymorphic forms called crystalline form 1, crystalline form 2 and crystalline form 3.

The procedure described in U.S. Pat. No. 5,877,187 generates a mixture of crystalline forms 2 and 3. We have discovered experimental conditions and specific solvents to produce clearly different polymorphic forms of bilastine. The crystalline form 1 of pure bilastine is prepared according to the procedures of this invention. The crystalline forms 1 and 2 are stable. Crystalline form 3 is not very stable and is difficult to obtain in the pure form. Both crystalline form 2 and crystalline form 3 are converted into crystalline form 1 by the procedures of this invention.

Crystalline form 1 of bilastine has a melting point of 200.3° C. Crystalline form 2 has a melting point of 205.2° C. Crystalline form 3 has a melting point of 197.0° C.

The crystalline form 1 of bilastine is also characterised by its infrared absorption spectrum in potassium bromide that has the following characteristic absorption bands, expressed in reciprocal centimetres:
3430 (s)*; 3057 (w)*; 2970 (s); 2929 (s); 2883 (m)*; 2857 (m); 2797 (w); 1667 (m); 1614 (m); 1567 (w); 1509 (s); 1481 (m); 1459 (vs)*; 1431 (m);1378 (w); 1346 (m); 1326 (m); 1288 (w); 1254 (m); 1199 (w); 1157 (w); 1121 (vs); 1045 (w); 1020 (w); 1010 (w); 991 (w); 973 (w); 945 (w); 829 (w); 742 (s); 723 (w); 630 (w), * where (w)=weak intensity,(m)=medium intensity, (s)=strong intensity, (vs)= very strong intensity. FIG. 1 represents the infrared spectrum of the crystalline form 1 of the bilastine in a potassium bromide tablet recorded in a Perkin Elmer Spectrum One FTIR spectrophotometer.

Figure 2:
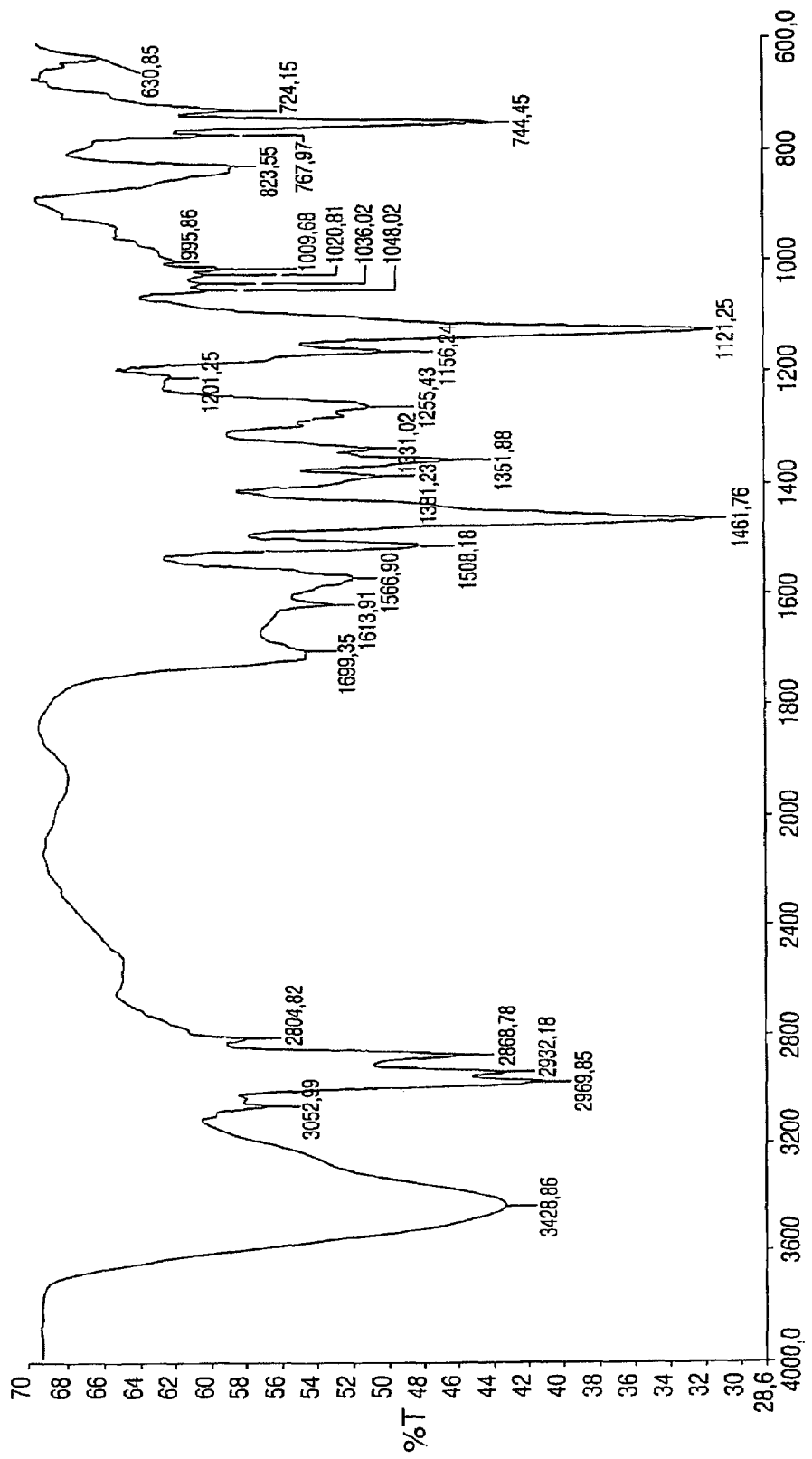
FIG. 2 shows a typical infrared absorption spectrum in potassium bromide of crystalline form 2. (Vertical axis: Transmission (%); Horizontal axis: Wavenumber ($cm^{-1}$)).

The crystalline form 2 of bilastine is also characterised by its infrared absorption spectrum in potassium that has the following characteristic absorption bands, expressed in reciprocal centimetres:

3429 (s)*; 3053 (w)*; 2970 (s)*; 2932 (s); 2868 (s); 2804 (w); 1699 (m); 1614 (m)*; 1567 (m); 1508 (s); 1461 (vs)*; 1381 (m); 1351 (s); 1331 (m); 1255 (m); 1201 (w); 1156 (m); 1121 (vs); 1048 (w); 995 (w); 823 (w); 767 (w); 744 (s); 724 (d); 630 (w), * where (w)=weak intensity, (m)=medium intensity, (s)=strong intensity, (vs)=very strong intensity. FIG. 2 represents the infrared spectrum of the crystalline form 2 of bilastine in a potassium bromide tablet recorded in a Perkin Elmer Spectrum One FTIR spectrophotometer.

Figure 3:
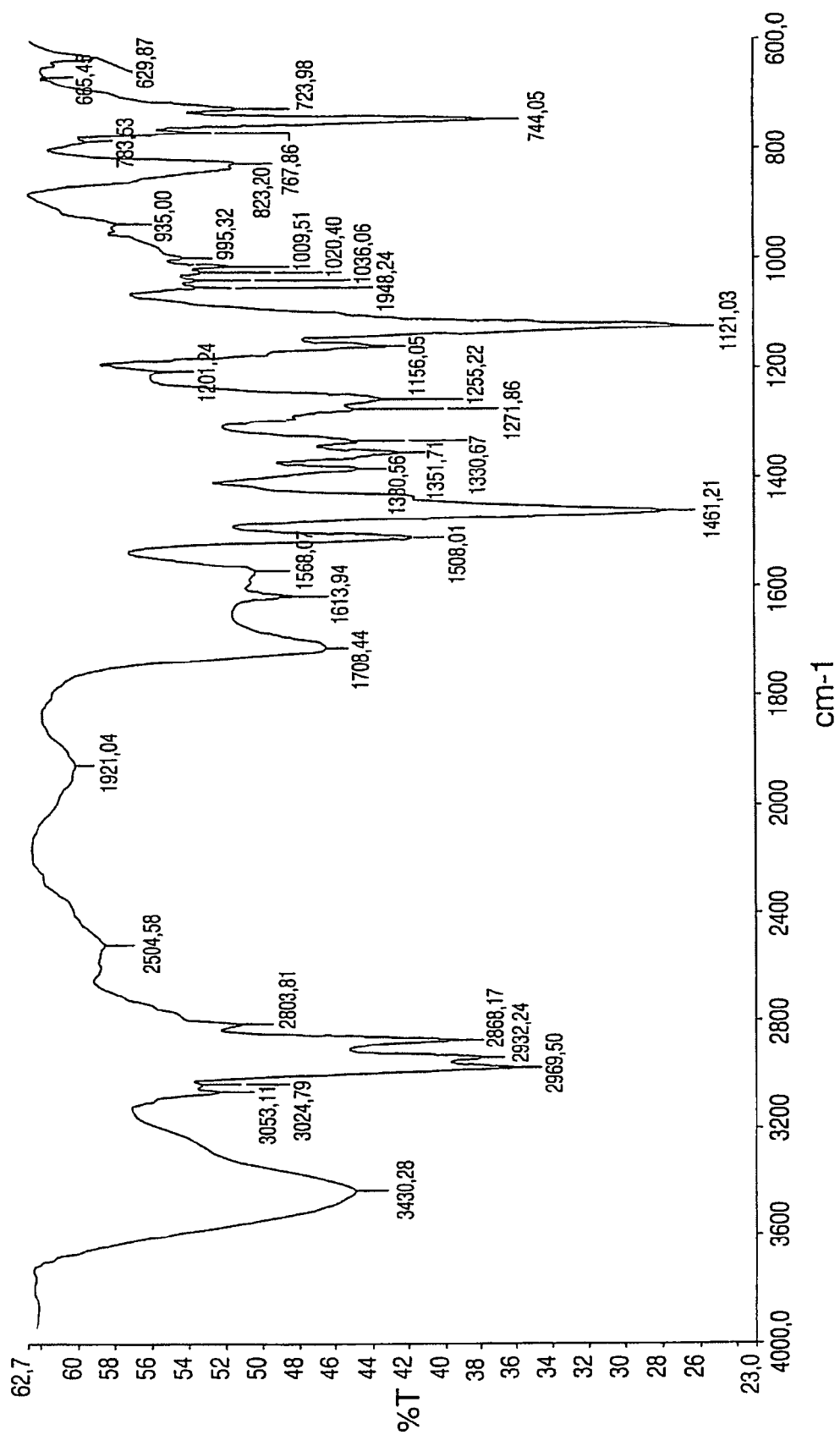
FIG. 3 shows a typical infrared absorption spectrum in potassium bromide of crstalline form 3. (Vertical axis: Transmission (%); Horizontal axis: Wavenumber ($cm^{-1}$)).

The crystalline form 3 of bilastine is also characterised by its infrared absorption spectrum in potassium bromide that has the following characteristic absorption bands, expressed in reciprocal centimeters:

3430 (s)*; 3053 (w)*; 2970 (s); 2932 (s); 2868 (s); 2804 (w); 1291 (w); 1708 (m)*; 1614 (m); 1568 (m); 1508 (s); 1461 (vs)*; 1380 (m); 1351 (m); 1330 (m); 1271 (m); 1255 (m), 1201 (w); 1156 (m); 1121 (vs); 1048 (w); 995 (w); 823 (m); 767 (w); 744 (s); 724 (w); 630 (w), * where (w)=weak intensity, (m)=medium intensity, (s)=strong intensity, (vs)= very strong intensity. FIG. 3 represents the infrared spectrum of the crystalline form 3 of the bilastine in a potassium bromide tablet recorded in a Perkin Elmer Spectrum One FTIR spectrophotometer.

We have discovered that, in selected experimental conditions, the mixture of the crystalline forms 2 and 3, obtained according to U.S. Pat. No. 5,877,187, is surprisingly transformed into crystalline form 1. We have also discovered that crystalline form 1 of bilastine is very stable and is not transformed into any of the other polymorphs 2 and 3. Similarly, in the same experimental conditions, the pure crystalline form 2 of bilastine is surprisingly transformed into the pure crystalline form 1. Crystalline form 3, which is the most unstable, undergoes the same transformation in the same conditions.

Crystalline form 1 of bilastine is a very stable polymorph at room temperature and is, therefore, very useful as an active ingredient of a pharmaceutical preparation. Crystalline form 1 is also stable when stored at, temperatures above room temperature.

The crystalline form 1 of bilastine is characterised by the following data of its X-ray crystallographic analysis as a monocrystal, with crystal parameters of approximately the following values:

| Crystallographic system | Monoclinic | |
|---|---|---|
| Spatial group | P2 (1)/c | |
| Crystal size | 0.56 × 0.45 × 0.24 mm | |
| Cell dimension | a = 23.38 (5) A angstrom | α = 90° |
| | b = 8.829 (17) A | β = 90° |
| | c = 12.59 (2) A | γ = 90° |
| Volume | 2600 A$^3$ | |
| Z, calculated density | 4, 1.184 mg/m$^3$ | |

During the development of crystalline form 1 of bilastine for pharmaceutical preparations, elaborated according to correct manufacturing procedures, we have discovered that crystallization of bilastine (prepared according to the description given in U.S. Pat. No. 5,877,187)from isopropylic alcohol and n-butanol leads to generation of the polymeric form 1 of bilastine with a high yield. Crystallization from acetone, dimethylsulfoxide, dimethylformamide, acetonitrile, and tetrahydrofurane or its mixtures thereof also lead to generation of crystalline form 1, although with lower yields. It is, therefore, preferable to use the former solvents.

The infrared spectrum of crystalline form 1 of bilastine in potassium bromide is characterised by the following bands, absent from polymorphs 2 and 3:

Wavelength (cm$^{-1}$)
3057
2929
2883
2857
2797
1667
1481
1431
1346
1326
1288
973
945
829

FIG. 1 shows the complete infrared spectrum of crystalline form 1 of bilastine in potassium bromide, recorded with a Perkin Elmer Spectrum One spectrophotometer.

Pharmaceutical Preparations

Pharmaceutical preparations of this invention can contain, as well as an effective quantity of crystalline form 1 of bilastine as an active ingredient as an antiallergic or antihistaminic agent, several pharmaceutically acceptable excipients. The solid pharmaceutical preparations include powders, tablets, dispersible granules, capsules, cachets and suppositories. A solid excipient can be one of several substances that act as diluents, aromatising agents, agglutinants or disintegrating agents and an encapsulation material. The powders and tablets preferentially contain from approximately 5 to approximately 20 per cent of the active ingredient. Appropriate solid excipients are magnesium carbonate, magnesium stearate, talc, sugar, lactose, pectin, dextrin, starch, gelatin, tragacanth, methylcellulose, sodium carboxymethylcellulose, waxes with low melting point, cocoa butter and similar products. The term "preparations" includes the formulation of the active ingredient with an excipient for encapsulation to produce a capsule in which the active ingredient (with or without other excipients) is surrounded with the excipient by an encapsulation material. Tablets, powders, cachets and capsules can be used as suitable forms for oral administration. The active ingredient can also be incorporated into a chewing gum that can contain sweeteners, flavorings and colorings as appropriate.

To prepare suppositories, a compound with a low melting point, such as a mixture of fatty acid glycerides or cocoa butter, is melted and the active ingredient is mixed well and homogeneously dispersed in the mixture with agitation. The homogeneous melted mixture is placed in the appropriate moulds and left to cool until it solidifies.

Liquid preparations comprise suspensions, that can be made by mixing the finely divided active ingredient in water with suspension agents.

Also, topical preparations are considered for nasal, ophthalmic and dermal use. Appropriate formulae for nasal administration can correspond to solutions or suspensions.

Ophthalmic formulae can be suspensions and ointments. Dermal preparations can be suspensions, ointments and creams. Ointments usually contain lipophylic excipients such as mineral oil or vaseline.

Similarly, a compound is being contemplated for transdermic use, consisting of a therapeutically effective amount of active ingredient incorporated into an excipient that corresponds to a liquid, a gel, a solid matrix or an adhesive patch sensitive to pressure, to be released via a transdermic administration system.

The effective antiallergic or antihistaminic amount of crystalline form 1 of bilastine for topical administration varies between 0.1 and 5% of the total weight of the pharmaceutical compound. The preferred amount ranges from 0.1 to 2% of the total weight of the pharmaceutical compound.

The effective antiallergic or antihistaminic amount of crystalline form 1 of bilastine for oral administration varies from 1 to 50 mg/day, with preferably an amount corresponding to approximately 2 to 20 mg/day in a single or fractionated doses.

Crystalline form 1 of bilastine has antihistaminic properties that have been demonstrated in experimental pharmacological models, such as preventing histamine-induced lethality in the guinea-pig and antagonism against cutaneous capillary permeability induced by histamine in the rat.

The following examples illustrate but do not limit the scope of the present invention.

EXAMPLE 1

Preparation of Crystalline Form 1 of Bilastine

Dissolve bilastine (see the U.S. Pat. No. 5,877,187) in isopropylic alcohol heated to reflux for approximately 15-20 minutes under nitrogen while stirring. Cool the solution to 50° C. over 6 hours and stop stirring. Let the solution cool to room temperature and stir again for three hours, filter and wash with cold isopropylic alcohol. Dry the solid residue in a vacuum oven at 35-40° C. to constant weight.

EXAMPLE 2

Preparation of Crystalline Form 1 of Bilastine

Heat a suspension of bilastine (see U.S. Pat. No. 5,877,187) in n-butanol and reflux for 3 hours under nitrogen while stirring. Leave the solution to cool while stirring, filter off the solid residue and dry it in a vacuum oven at 35-40° C. to constant weight.

EXAMPLE 3

Preparation of Crystalline Form 1 of Bilastine

Treat a mixture of polymorphs 2 and 3 of bilastine for several hours with hot acetone. Let the mixture cool to room temperature and filter off the solid residue. Dry it to constant weight.

EXAMPLE 4

Preparation of Crystalline Form 1 of Bilastine

Dissolve crystalline form 3 of bilastine in isopropylic alcohol heated to reflux and stir for approximately 15-20 minutes under nitrogen. Let the solution reach room temperature constantly stirring, filtering and washing with cold isopropanol. Dry the solid in a vacuum oven at 35-40° C. to constant weight.

EXAMPLE 5

Preparation of Crystalline Form 1 of Bilastine

Dissolve crystalline form 2 of bilastine in n-butanol heated to reflux while stirring for approximately 3 hours. Let the solution reach room temperature while stirring, filtering and draining. Dry the solid in a vacuum oven at 35-40° C. to constant weight.

The invention claimed is:

1. A crystalline form 1 of bilastine having, upon X-ray crystallography analysis, crystal parameters of substantially the following:

| Crystallographic system | Monoclinic | |
|---|---|---|
| Spatial group | P2 (1)/c | |
| Crystal size | 0.56 × 0.45 × 0.24 mm | |
| Cell dimension | a = 23.38 (5) A angstrom | $\alpha = 90°$ |
| | b = 8.829 (17) A | $\beta = 90°$ |
| | c = 12.59 (2) A | $\gamma = 90°$ |
| Volume | 2600 A$^3$ | |
| Z, calculated density | 4, 1.184 mg/m$^3$, | | an infrared spectrum in potassium bromide with the following bands:
Wavenumber (cm$^{-1}$)
3057
2929
2883
2857
2797
1666
1481
1431
1346
1326
1288
1020
973
945
829 and an infrared spectrum in potassium bromide which is substantially identical to that shown in FIG. 1.

2. A process for preparing the crystalline form 1 of bilastine according to claim 1, wherein said process comprises:
 a) combining bilastine with a solvent selected from the group consisting of isopropylic alcohol, n-butanol and acetone to form a mixture and heating the mixture to a reflux temperature of said solvent;
 b) letting the mixture cool to room temperature;
 c) filtering off solid residue from said cooled mixture; and
 d) drying said solid residue to a constant weight.

3. A process for preparing the crystalline form 1 of bilastine according to claim 1, wherein said process comprises:
 a) combining crystalline form 2 of bilastine, or crystalline form 3 of bilastine, or a mixture thereof with a solvent selected from the group consisting of isopropylic alcohol, n-butanol and acetone to form a mixture and heating the bilastine/solvent mixture to a reflux temperature of the solvent;
 b) letting the mixture cool to room temperature;
 c) filtering off solid residue from said cooled mixture; and
 d) drying said solid residue to a constant weight.

4. A solid antihistiminic pharmaceutical composition comprising the crystalline form 1 of bilastine according to claim 1 as an active ingredient together with at least one excipient.

5. A process for treating allergic diseases in a patient in need thereof, wherein the process comprises administering to said patient a pharmaceutical composition according to claim 4.

6. A process for treating allergic diseases in a patient in need thereof, wherein the process comprises administering to said patient an effective amount of crystalline form 1 of bilastine in a solid pharmaceutical composition according to claim 4.

* * * * *

UNITED STATES PATENT AND TRADEMARK OFFICE
CERTIFICATE OF CORRECTION

PATENT NO. : 7,612,095 B2 Page 1 of 1
APPLICATION NO. : 10/511822
DATED : November 3, 2009
INVENTOR(S) : Orjales Venero et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 843 days.

Signed and Sealed this

Nineteenth Day of October, 2010

David J. Kappos
*Director of the United States Patent and Trademark Office*